United States Patent [19]

Balzer et al.

[11] Patent Number: 5,382,702
[45] Date of Patent: Jan. 17, 1995

[54] PROCESS FOR THE PRODUCTION OF 5-ALKOXY-2,4-DINITRO-ALKYLBENZENES

[75] Inventors: Wolfgang R. Balzer; Thomas Clausen, both of Alsbach; Alexa Weinges, Heidelberg, all of Germany

[73] Assignee: Wella Aktiengesellschaft, Darmstadt, Germany

[21] Appl. No.: 142,383
[22] PCT Filed: Mar. 20, 1993
[86] PCT No.: PCT/EP93/00678
§ 371 Date: Nov. 19, 1993
§ 102(e) Date: Nov. 19, 1993
[87] PCT Pub. No.: WO93/25512
PCT Pub. Date: Dec. 23, 1993

[30] Foreign Application Priority Data

Jun. 17, 1992 [DE] Germany ............... 4219755

[51] Int. Cl.⁶ ............... C07C 43/205; C07C 205/37
[52] U.S. Cl. ............... 568/584; 568/583
[58] Field of Search ............... 568/583, 584

[56] References Cited

U.S. PATENT DOCUMENTS 4,537,999  8/1985  Ogawa et al. ............... 568/584

FOREIGN PATENT DOCUMENTS 0204111  12/1986  European Pat. Off. .
0252351  1/1988  European Pat. Off. .
1121453  7/1968  United Kingdom ............... 568/584
9204005  3/1992  WIPO .

OTHER PUBLICATIONS

Journal of the chemical society, Perkin Transactions Feb. 1972, John F. Corbett pp. 999–1005.

*Primary Examiner*—Werren B. Lone
*Attorney, Agent, or Firm*—Michael J. Striker

[57] ABSTRACT

Process for producing 5-alkoxy-2,4-dinitroalkylbenzenes of the general formula (I)

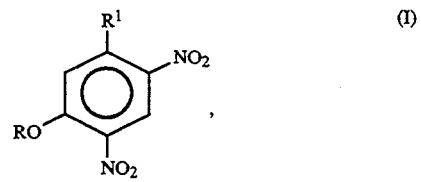

$R^1 = C_1$ to $C_4$ alkyl;
$R = C_1$ to $C_6$ alkyl group, $C_2$ to $C_4$ hydroxyalkyl, $C_3$ to $C_4$ dihydroxyalkyl, in which a 3-fluoroalkylbenzene is nitrated and the obtained 2,4-dinitro-5-fluoroalkylbenzene is then reacted with a suitable alcohol at $-5°$ C. to $+25°$ C. with the addition of sodium hydroxide or potassium hydroxide.

7 Claims, No Drawings

PROCESS FOR THE PRODUCTION OF 5-ALKOXY-2,4-DINITRO-ALKYLBENZENES

BACKGROUND OF THE INVENTION

The present invention relates to processes for producing 5-alkoxy-2,4-dinitroalkylbenzenes of the general formula (I)

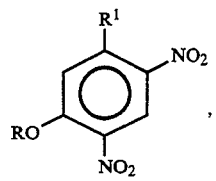

where $R^1$ is a branched or unbranched $C_1$ to $C_4$ alkyl group and R is a branched or unbranched $C_1$ to $C_6$ alkyl group, a $C_2$ to $C_4$ hydroxyalkyl group or a $C_3$ to $C_4$ dihydroxyalkyl group, which can be used as dye precursor, etc., e.g. for hair dyes.

A number of processes for producing 5-alkoxy-2,4-dinitroalkylbenzenes of formula (I) are already known from the relevant literature. However, these processes are unsatisfactory in many respects.

For example, J. F. Corbett, Journal of the Chemical Society Perkin II, page 999 (1972), describes a process for producing 5-methoxy-2,4-dinitrotoluene in which 5-chloro-2,4-dinitrotoluene and methanol are heated under reflux in the presence of potassium hydroxide. However, the yield in this process is unsatisfactory.

Further, DE-OS 3 622 784 describes a process for the production of 5-alkoxy-2,4-dinitroalkylbenzenes in which 5-alkyl-2,4-dinitrophenol is reacted in an appropriate solvent with a suitable alkyl halide in the presence of a base and the product is then precipitated by adding water. Although the alkylation in this process produces satisfactory yields (50 to 77%), the overall production method involves some disadvantages. For example, the starting material required for this method must be produced by a three-step synthesis starting with 3-methyl-6-nitrophenol by introducing a mesyl protective group, nitration and subsequent separation of the protective group with a total yield of roughly 76%. Further, the alkyl halides, which are not without disadvantages, must be used as reagents for producing the alkyl compounds. Although the process described above for producing 5-alkoxy-2,4-dinitroalkylbenzenes of the general formula (I) can be carried out with a satisfactory yield technically, it nevertheless has disadvantages in economical and ecological respects. The large number of required reaction steps and the type of reagents that are used necessitate a high input of energy for carrying out the reactions. In addition, waste products are produced in every reaction step (by-products and solvent) which must be worked up and disposed of in an expensive manner to prevent additional environmental loading. These disadvantages are also shared in great measure by the process according to Corbett in which the proportion of by-products is greater than the proportion of desired reaction products.

SUMMARY OF THE INVENTION

Therefore, it is an object of the present invention to provide a process for the production of 5-alkoxy-2,4-dinitroalkylbenzenes of the formula (I) which enables a simple and economical production of these compounds and in which the aforementioned disadvantages are avoided.

Surprisingly, it has now been found that the proposed object is met in an outstanding manner in that the 5-alkoxy-2,4-dinitroalkylbenzenes of the general formula (I) are produced at low temperatures by nucleophilic substitution of 2,4-dinitro-5-fluoroalkylbenzenes.

The subject matter of the present invention is therefore a process for producing 5-alkoxy-2,4-dinitroalkylbenzenes of the general formula (I)

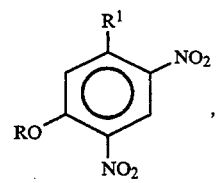

where $R^1$ is a branched or unbranched $C_1$ to $C_4$ alkyl group and R is a branched or unbranched $C_1$ to $C_6$ alkyl group, a $C_2$ to $C_4$ hydroxyalkyl group or a $C_3$ to $C_4$ dihydroxyalkyl group, in which a 3-fluoroalkylbenzene (II) is nitrated and the obtained 2,4-dinitro-5-fluoroalkylbenzene (III) is reacted with a suitable alcohol at $-5°$ C. to $+25°$ C. with the addition of sodium hydroxide or potassium hydroxide according to the following general reaction sequence:

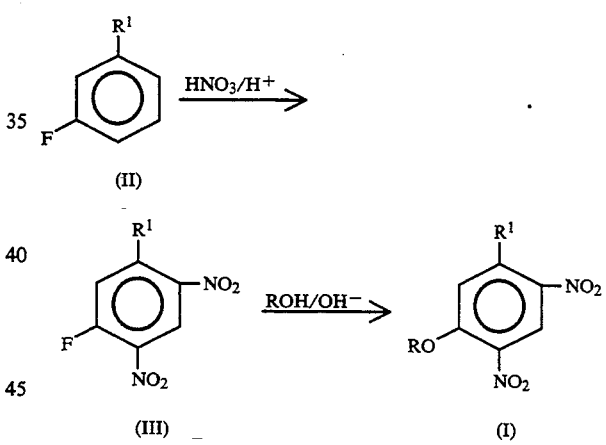

In the process according to the invention, a 3-fluoroalkylbenzene of the general formula (II) is first nitrated according to the methods known from DE-OS 40 28 661. The obtained 2,4-dinitro-5-fluoroalkylbenzene of formula (III) is then reacted with a suitable alcohol and sodium hydroxide or potassium hydroxide at a temperature of $-5°$ C. to $+25°$ C., preferably at a temperature of $0°$ C. to $+10°$ C., accompanied by rigorous stirring and the alcohol serves as both reagent and solvent simultaneously and is therefore used in a multiple molar excess.

Monohydroxyalkyl compounds with 1 to 4 carbon atoms in the alkyl chain as well as dihydroxyalkyl compounds with 2 to 4 carbon atoms in the alkyl chain or trihydroxyalkyl compounds with 3 or 4 carbon atoms in the alkyl chain can be used as alcohols. The use of methanol, ethanol and ethylene glycol is particularly preferred.

The sodium hydroxide or potassium hydroxide can be used in equimolar amounts with respect to the 2,4- dinitro-5-fluoroalkylbenzene as well as in a molar excess. A molar excess of sodium hydroxide or potassium hydroxide is preferred.

A molar ratio of 2,4-dinitro-5-fluoroalkylbenzene to sodium hydroxide or potassium hydroxide of 1:1.4 is particularly preferred.

3-Fluorotoluene, from which 2,4-dinitro-5-fluorotoluene is obtained by nitration, is preferably used as 3-fluoroalkylbenzene of formula (II).

In the test method described above, a good yield of the 5-alkoxy-2,4-dinitroalkylbenzene of formula (I) is obtained, whereas the use of 2,4-dinitro-5-chloroalkylbenzenes or 2,4-dinitro-5-bromoalkylbenzenes instead of the 2,4-dinitro-5-fluoroalkylbenzenes according to the invention produces the compounds of formula (I) only in low yields or in a highly impure form.

Surprisingly, carrying out the process according to the invention at temperatures higher than those indicated also leads to a distinctly lower yield. For example, the yield is reduced by a fourth to a third when the reaction of 2,4-dinitro-5-fluoroalkylbenzene with alcohol is carried out at temperatures higher than −5° C. to +25° C. (e.g. under reflux).

The subject matter of the invention is explained in more detail in the following examples, but is not limited to these examples.

EXAMPLES

Example 1

5-methoxy-2,4-dinitrotoluene 2.8 g (14 mmoles) 2,4-dinitro-5-fluorotoluene produced by nitration of 3-fluorotoluene according to Example A, Step 1, of DE-OS 40 28 661 are dissolved in 100 ml methanol and a mixture of 1.12 g (20 mmoles) potassium hydroxide powder and 20 ml methanol is slowly added to this at different temperatures accompanied by rigorous stirring. The reaction mixture is then poured over water, the obtained precipitate is removed by filtration and recrystallized from isopropanol.

The melting point is 101° C.

The following yields are obtained depending on the reaction temperature:

| reaction temperature | yield % of theory |
| --- | --- |
| reflux (>65° C.) | 38 |
| room temperature (20–25° C.) | 51 |
| ice cooling (0–10° C.) | 71 |

Example 2

5-ethoxy-2,4-dinitrotoluene 2.8 g (14 mmoles) 2,4-dinitro-5-fluorotoluene produced by nitration of 3-fluorotoluene according to Example A, Step 1, of DE-OS 40 28 661 are dissolved in 100 ml ethanol and a mixture of 1.12 g (20 mmoles) potassium hydroxide powder and 20 ml ethanol is slowly added to this at different temperatures accompanied by rigorous stirring. The reaction mixture is then poured over water, the obtained precipitate is removed by filtration and recrystallized from isopropanol.

The melting point is 95° to 96° C.

The following yields are obtained depending on the reaction temperature:

| reaction temperature | yield % of theory |
| --- | --- |
| reflux (roughly 80° C.) | 25 |
| room temperature (20–25° C.) | 39 |
| ice cooling (0–10° C.) | 76 |

All percentages shown in the present application are percent by weight unless otherwise indicated.

While the invention has been illustrated and described as embodied in a process for producing 5-alkoxy-2,4-dinitroalkylbenzenes, it is not intended to be limited to the details described above in the examples, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

1. Process for producing 5-alkoxy-2,4-dinitroalkylbenzenes of the formula (I)

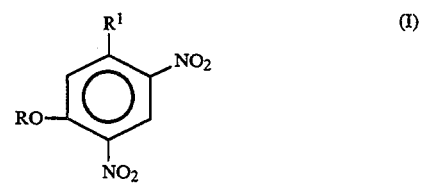

wherein $R^1$ is a member selected from the group consisting of $C_1$ to $C_4$ alkyl groups and R is a member selected from the group consisting of $C_1$ to $C_6$ alkyl groups, $C_2$ to $C_4$ hydroxylalkyl groups and $C_3$ to $C_4$ dihydroxyalkyl groups, said process comprising the steps of:

a) nitrating a 3-fluoroalkylbenzene to form a 2,4-dinitro-5-fluoroalkylbenzene; and then b) reacting said 2,4-dinitro-5-fluoroalkylbenzene with an alcohol and a hydroxide-containing base selected from the group consisting of sodium hydroxide and potassium hydroxide at −5° C. to +25° C.

2. Process as defined in claim 1, wherein said reacting of said 2,4-dinitro-5-fluoroalkylbenzene with said alcohol and said hydroxide-containing base takes place at 0° C. to +10° C.

3. Process as defined in claim 1, wherein said 2,4-dinitro-5-fluoroalkylbenzene is 2,4-dinitro-5-fluorotoluene.

4. Process as defined in claim 1, wherein said alcohol is selected from the group consisting of methanol, ethanol and ethylene glycol.

5. Process as defined in claim 4, wherein said alcohol is present in molar excess relative to said 2,4-dinitro-5-fluoroalkylbenzene.

6. Process as defined in claim 1, wherein a molar ratio of said 2,4-dinitro-5-fluoroalkylbenzene to said hydroxide containing base is 1:1.4.

7. Process for producing 5-alkoxy-2,4-dinitroalkylbenzenes of the formula (I)

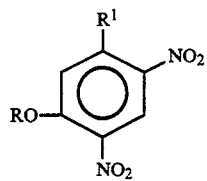
(I)

wherein R[1] is a member selected from the group consisting of $C_1$ to $C_4$ alkyl groups and R is a member selected from the group consisting of $C_1$ to $C_6$ alkyl groups, $C_2$ to $C_4$ hydroxylalkyl groups and $C_3$ to $C_4$ dihydroxyalkyl groups, said process comprising the steps of:

a) mixing 3-fluoroalkylbenzene with concentrated nitric acid to form a 2,4-dinitro-5-fluoroalkylbenzene; and then b) reacting said 2,4-dinitro-5-fluoroalkylbenzene with a molar excess of alcohol selected from the group consisting of methanol, ethanol and ethylene glycol and a molar excess of a hydroxide-containing base selected from the group consisting of sodium hydroxide and potassium hydroxide at −5° C. to +25° C., said molar excess of said alcohol and said molar excess of said hydroxide-containing base being relative to said 2,4-dinitro-5-fluoroalkylbenzene.

* * * * *